United States Patent [19]

Merger et al.

[11] Patent Number: 5,254,752

[45] Date of Patent: Oct. 19, 1993

[54] PREPARATION OF 4-HALOBENZYL ALCOHOLS

[75] Inventors: Franz Merger, Frankenthal; Martin Brudermueller, Mannheim; Martin Schmidt-Radde, Ludwigshafen, all of Fed. Rep. of Germany

[73] Assignee: BASF Aktiengesellschaft, Ludwigshafen, Fed. Rep. of Germany

[21] Appl. No.: 960,774

[22] Filed: Oct. 14, 1992

[30] Foreign Application Priority Data

Oct. 18, 1991 [DE] Fed. Rep. of Germany ....... 4134497

[51] Int. Cl.$^5$ .................... C07C 29/141; C07C 27/04
[52] U.S. Cl. ..................... 568/812; 568/814
[58] Field of Search ................. 568/812, 814, 862

[56] References Cited

U.S. PATENT DOCUMENTS

| 3,527,817 | 8/1970 | Dietzler et al. | 568/812 |
| 4,704,480 | 11/1987 | Gefri et al. | 568/396 |
| 4,783,559 | 11/1988 | Matsushita | 568/812 |

FOREIGN PATENT DOCUMENTS

| 1643876 | 1/1971 | Fed. Rep. of Germany | 568/812 |
| 175238 | 11/1922 | United Kingdom | 568/396 |
| 1159967 | 7/1969 | United Kingdom | 568/396 |

OTHER PUBLICATIONS

Kajitani et al, Bulletin of the Chem. Soc. of Japan, vol. 52, No. 8, 1979, pp. 2343-2348.

Primary Examiner—Werren B. Lone
Attorney, Agent, or Firm—John H. Shurtleff

[57] ABSTRACT

The invention provides a process for the preparation of a 4-halobenzyl alcohol of the formula

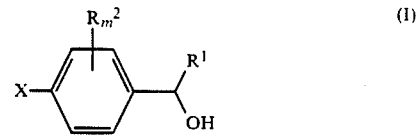

(I)

where
$R^1$ is hydrogen, $C_1$- to $C_{20}$-alkyl, $C_2$- to $C_{20}$-alkoxyalkyl, $C_3$- to $C_{20}$-cycloalkyl, or $C_4$- to $C_{30}$-cycloalkylalkyl,
$R^2$ is $C_1$- to $C_{20}$-alkyl, $C_2$- to $C_{20}$-alkoxyalkyl, $C_3$- to $C_{20}$-cycloalkyl or $C_4$- to $C_{30}$-cycloalkylalkyl,
X is halogen and
m is 0 to 2, by reacting a haloaromatic carbonyl compound of the formula

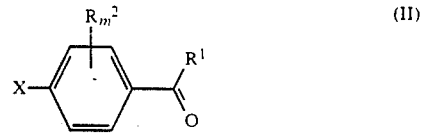

(II)

where $R^1$, $R^2$, X and m are as defined above, with hydrogen on a hydrogenation catalyst consisting essentially of copper oxide (I), copper oxide (II) and mixtures thereof in the presence of at least one primary, secondary or tertiary amine selected from the group consisting of acyclic, cyclic and heterocyclic aliphatic amines, in the presence or absence of an inert solvent, at from 50° to 130° C. and at from 10 to 200 bar.

14 Claims, No Drawings

PREPARATION OF 4-HALOBENZYL ALCOHOLS

The present invention relates to a process for the preparation of 4-halobenzyl alcohols by catalytic hydrogenation of haloaromatic carbonyl compounds in the presence of copper oxide catalysts.

The catalytic hydrogenation of haloaromatic carbonyl compounds in the presence of copper chromite catalysts is disclosed in DE-A-16 43 876 and U.S. Pat. No. 3,527,817. Hydrogenation of ortho-chlorophenyl ketones or mixtures thereof with meta- or para-chlorinated isomers or with dichlorinated compounds on copper chromite catalysts at higher temperatures than in the case of halogen-free compounds to give the corresponding carbinols only proceeds at an acceptable rate if alkaline earth metal hydroxides are present. The presence of other basic compounds alone has no effect, or even an inhibiting effect, on the hydrogenation. Only addition of amines having a pKa of at least 3.7 in addition to the alkaline earth metal hydroxides accelerates the hydrogenation of ortho-chlorophenyl ketones.

The process described in DE-A-16 43 876 has the following disadvantages:

The hydrogenation is carried out at temperatures which are higher than in the case of halogen-free carbonyl compounds, namely at from 100° to 175° C., preferably above 150° C.;

the addition of amines is only possible in combination with alkaline earth metal hydroxides;

the catalysts contain chromium;

the use of alkaline earth metal hydroxide causes considerable problems for continuous hydrogenation since the fact that the alkaline earth metal hydroxides are only sparingly soluble or insoluble in the reaction medium means that a process of this type cannot be introduced industrially, and furthermore deposits cause rapid deactivation of the catalysts (short catalyst life).

It is an object of the present invention to overcome the abovementioned disadvantages.

We have found that this object is achieved by a novel and improved process for the preparation of 4-halobenzyl alcohols of the formula I

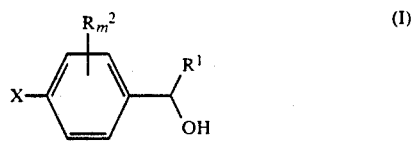

where
$R^1$ is hydrogen, $C_1$- to $C_{20}$-alkyl, $C_2$- to $C_{20}$-alkoxyalkyl, $C_3$- to $C_{20}$-cycloalkyl, or $C_4$- to $C_{30}$-cycloalkylalkyl,
$R^2$ is $C_1$- to $C_{20}$-alkyl, $C_2$- to $C_{20}$-alkoxyalkyl, $C_3$- to $C_{20}$-cycloalkyl or $C_4$- to $C_{30}$-cycloalkylalkyl,
X is halogen and
m is 0 to 2,
which comprises reacting haloaromatic carbonyl compounds of the formula II

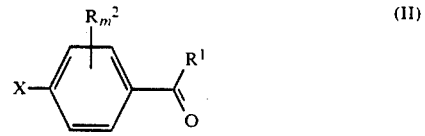

where $R^1$, $R^2$, X and m are as defined above, with hydrogen in the presence of an amine on copper catalysts, in the presence or absence of an inert solvent, at from 50° to 130° C. and at from 10 to 200 bar.

The process according to the invention can be carried out as follows:

The haloaromatic carbonyl compound II can be reacted with hydrogen at from 50° to 130° C., preferably from 70° to 100° C., under autogenous pressure or by injection of hydrogen, ie. at from 10 to 200 bar, preferably at from 50 to 150 bar, on a copper catalyst in the presence of an amine and in the presence or absence of an inert solvent.

The hydrogenation can be carried out batchwise or preferably continuously in the liquid phase or gas phase, in tubular or stirred reactors, either with upward or downward flow through catalysts in suspension, preferably in a fixed bed, at a weight hourly space velocity at from 0.05 to 1 kg of feed mixture/(kg of catalyst per hour), preferably at from 0.05 to 0.3 kg of feed mixture/(kg of catalyst per hour).

Suitable copper catalysts are those whose catalytically active material comprises from 70 to 100% by weight, preferably from 85 to 100% by weight, in particular from 95 to 100% by weight, of copper oxide and which contain essentially no chromium oxide. The copper oxide catalysts may contain from 0 to 30% by weight, preferably from 0 to 15% by weight, particularly preferably from 0 to 5% by weight, of catalytically active material. Suitable copper oxides are copper(I) oxide and copper(II) oxide and mixtures thereof. The copper catalysts can be employed as unsupported catalysts or preferably on inert support materials, such as aluminum oxide, silica, titanium oxide, zirconium oxide, magnesium silicate or oxides of the elements from main groups three and four.

The feed mixture may contain, for example, from 40 to 80% by weight of a haloaromatic carbonyl compound II, from 15 to 55% by weight of an inert solvent and from 1 to 10% by weight of an amine. The amount of amine added should in general be not less than 1% by weight, based on the haloaromatic carbonyl compound II, i.e. from 1 to 10% by weight, preferably 1.5 to 5% by weight.

The haloaromatic carbonyl compound II can preferably be reacted dissolved in an inert solvent. Suitable inert solvents are ethers, e.g. tetrahydrofuran, dioxane, dibutyl ether, dipropyl ether and diethyl ether, inert hydrocarbons, such as toluene and xylene, but preferably alcohols, such as $C_1$- to $C_{20}$-alkanols, preferably $C_1$- to $C_8$-alkanols, such as methanol, ethanol, n-propanol, i-propanol and n-butanol, particularly preferably ethanol.

Suitable amines are primary, secondary and tertiary, acyclic, cyclic and heterocyclic amines, such as $C_1$- to $C_{20}$-alkylamines, eg. methylamine, dimethylamine, trimethylamine, ethylamine, diethylamine, triethylamine, propylamine, dipropylamine, tripropylamine, butylamine, dibutylamine, tributylamine, pentylamine, dipentylamine, hexylamine, heptylamine, octylamine, nonylamine, decylamine and dodecylamine, preferably triethylamine, diethylamine, hexadecylamine and octadecylamine, $C_1$- to $C_{20}$-monoalkanolamines, eg. dimethyl (hydroxyethyl) amine and methyl(hydroxyethyl)amine, $C_2$- to $C_{20}$-dialkanolamines, e.g. methylbis(hydroxyethyl)amine, and heterocyclic amines, e.g. pyridine, morpholine, quinoline, piperidine, piperazine and derivatives thereof containing one to five $C_1$- to $C_8$-alkyl groups, preferably containing one to three $C_1$- to $C_4$-alkyl groups, such as methyl, ethyl, n-propyl, isopropyl, n-butyl, isobutyl, sec-butyl and tert-butyl. It is also possible to employ mixtures of various of the abovementioned amines.

The process according to the invention for the hydrogenation of haloaromatic carbonyl compounds proceeds under significantly milder reaction conditions on chromium-free copper oxide catalysts. Furthermore, if an amine is added as base, the hydrogenation proceeds without the use of solid reaction additives which are industrially impracticable, such as inorganic bases, e.g. alkali metal hydroxides and alkaline earth metal hydroxides, which result in heterogeneous reaction mixtures.

During the novel hydrogenation of, for example, p-chloroacetophenone under pressure in the presence of from 2 to 10% by weight of an amine and from 15 to 55% by weight of ethanol as solvent, no deactivation of the copper oxide catalysts had occurred after an operating time of more than 900 hours.

The reaction products can be separated from the added amine and the solvent by distillation, and both the amine and the solvent can be fed back into the hydrogenation. The haloaromatic carbonyl compounds II are known from Houben-Weyl, Methoden der organischen Chemie, vol. 7/2a, pp. 39ff, and can be prepared by the processes described therein.

$R^1$, $R^2$, X and m are defined as follows:

$R^1$ and $R^2$ - independently of one another are $C_1$- to $C_{20}$-alkyl, preferably $C_1$- to $C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl and isododecyl, particularly preferably $C_1$- to $C_4$-alkyl, such as methyl, ethyl, n-propyl, isopropyl, n-butyl, isobutyl, sec-butyl or tert-butyl, $C_2$- to $C_{20}$-alkoxyalky, preferably $C_2$- to $C_8$-alkoxyalkyl, such as methoxymethyl, ethoxymethyl, n-propoxymethyl, isopropoxy-methyl, n-butoxymethyl, isobutoxymethyl, sec-butoxymethyl, tert-butoxymethyl, 1-methoxyethyl or 2-methoxyethyl, $C_1$- to $C_{20}$-cycloalkyl, preferably $C_3$- to $C_8$-cycloalkyl, such as cyclopropyl, cyclobutyl, cyclopentyl, cyclohexyl, cycloheptyl or cyclooctyl, particularly preferably cyclopentyl, cyclohexyl or cyclo-octyl, $C_4$- to $C_{30}$-cycloalkylalkyl, preferably $C_4$-to $C_{20}$-cycloalkylalkyl, such as cyclopentylmethyl, $R^1$ is additionally hydrogen, x is halogen, such as fluorine, chlorine, bromine or iodine, preferably chlorine or bromine, particularly preferably chlorine, m is an integer from 0 to 2, such as 0, 1 or 2, particularly preferably 0 or 1, $R^3$, $R^4$ and $R^5$ are hydrogen, $C_1$- to $C_{20}$-alkyl, preferably $C_1$- to $C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl or isododecyl, particularly preferably $C_1$- to $C_4$-alkyl, such as methyl, ethyl, n-propyl, isopropyl, n-butyl, isobutyl, sec-butyl or tert-butyl, at least one of the radicals $R^3$, $R^4$ and $R^5$ being different from hydrogen.

The 4-halobenzyl alcohols I are intermediates in the preparation of substituted styrenes (U.S. Pat. No. 3,927,133, Org. Synthesis Collective Volume 3, 204–206).

EXAMPLES

EXAMPLE 1

A solution of 65% by weight of 4-chloroacetophenone, 30% by weight of ethanol and 5% by weight of triethylamine was reacted in a tubular reactor on a copper oxide/aluminum oxide catalyst (45/55; 3 mm pellets) at a weight hourly space velocity of 0.16 kg/(kg of catalyst per hour) at 90° C. and a hydrogen pressure of bar. After an operating time of 900 hours under constant experimental conditions, the conversion is 99% at a selectivity of 99% (GC area %).

EXAMPLE 2

A solution of 63% by weight of 4-chloroacetophenone, 30% by weight of ethanol and 2% by weight of diethylamine was reacted in a tubular reactor on a copper oxide/aluminum oxide catalyst (45/55; 3 mm pellets) at a weight hourly space velocity of 0.16 kg/(kg of catalyst per hour) at 90° C. and a hydrogen pressure of 100 bar. After an operating time of 68 hours under constant experimental conditions, the conversion is 98% at a selectivity of >99% (GC area %).

EXAMPLE 3

As for Example 2, but with n-butylamine in place of diethylamine. After an operating time of 20 hours under constant experimental conditions, the conversion is 69% at a selectivity of 80% (GC area %).

EXAMPLE 4

A solution of 62% by weight of 4-chloroacetophenone, 25% by weight of methanol and 3% by weight of triethylamine was reacted in a tubular reactor on a copper oxide/aluminum oxide catalyst (45/55; 3 mm pellets) at a weight hourly space velocity of 0.12 kg/(kg of catalyst per hour) at 120° C. and a hydrogen pressure of 100 bar. After an operating time of 33 hours under constant experimental conditions, the conversion is 85% at a selectivity of 98% (GC area %).

EXAMPLE 5

As for Example 4, but with tetrahydrofuran. After an operating time of 24 hours under constant experimental conditions, the conversion is 77% and the selectivity is 99% (GC area %).

EXAMPLE 6

A solution of 75% by weight of 4-chloroacetophenone and 25% by weight of ethanol was reacted in a tubular reactor on a copper oxide/aluminum oxide catalyst (45/55; 3 mm pellets) at a weight hourly space velocity of 0.12 kg/(kg of catalyst per hour) at 90° C. and a hydrogen pressure of 100 bar. After an operating time of 48 hours under constant experimental conditions, the conversion is 54% at a selectivity of >99% (GC area %).

EXAMPLE 7

A solution of 97% by weight of 4-chloroacetophenone and 3% by weight of triethylamine was reacted in a tubular reactor on a copper oxide/aluminum oxide catalyst (45/55; 3 mm pellets) at a weight hourly space velocity of 0.12 kg/(kg of catalyst per hour) at 120° C. and a hydrogen pressure of 100 bar. After an operating time of 39 hours under constant experimental conditions, the conversion is 58% at a selectivity of >99% (GC area %).

EXAMPLE 8

A solution of 30% by weight of 4-chlorobenzaldehyde, 68% by weight of ethanol and 2% by weight of triethylamine was reacted in a tubular reactor on a copper oxide/aluminum oxide catalyst (45/55; 3 mm pellets) at a weight hourly space velocity of 0.16 kg/(kg of catalyst per hour) at 90° C. and a hydrogen pressure of 100 bar. After an operating time of 26 hours under constant experimental conditions, the conversion is 97% at a selectivity of >99% (GC area %).

We claim:

1. A process for the preparation of a 4-halobenzyl alcohol of the formula

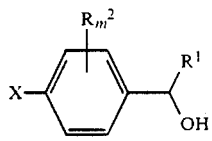

where
R$^1$ is hydrogen, C$_1$- to C$_{20}$- alkyl, C$_2$-to C$_{20}$-alkoxyalkyl, C$_2$- to C$_{20}$-cycloalkyl, or C$_4$- to C$_{30}$-alkoxyalkyl,
R$^2$ is C$_1$- to C$_{20}$-alkyl, C$_2$- to C$_{20}$- alkoxyalkyl, C$_3$- to C$_{20}$-cycloalkyl or C$_4$- to C$_{30}$-cycloalkylalkyl,
X is halogen and
m is 0 and 2,
which comprises:
reacting a haloaromatic carbonyl compound of the formula

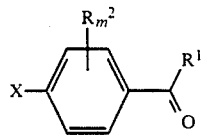

where R$^1$, R$^2$, X and m are as defined above, with hydrogen on a hydrogenation catalyst containing copper oxide (I), copper oxide (II) or mixtures thereof in the presence of at least one primary, secondary or tertiary amine selected from the group consisting of acyclic, cyclic and heterocyclic aliphatic amines, and mixtures thereof, and in the presence or absence of an inert solvent, at from 50° to 130° C. and at from 10 to 200 bar.

2. A process for the preparation of 4-halobenzyl alcohols of the formula I as claimed in claim 1, wherein the reaction is carried out at from 70° to 100° C. and at from 50 to 150 bar.

3. A process for the preparation of 4-halobenzyl alcohols of the formula I as claimed in claim 1, wherein the reaction is carried out continuously.

4. A process for the preparation of 4-halobenzyl alcohols of the formula I as claimed in claim 1, wherein the inert solvent employed is a C$_1$- to C$_{20}$-alkanol.

5. A process for the preparation of 4-halobenzyl alcohols of the formula I as claimed in claim 1, wherein the amine employed is an aliphatic amine of the formula NR$^3$R$^4$R$^5$ where R$^3$, R$^4$ and R$^5$ are hydrogen or C$_1$- to C$_{20}$-alkyl.

6. A process as claimed in claim 1, wherein said amine is selected from the group consisting of alkylamines, cycloalkylamines, mono- and di-alkanolamines, and a heterocyclic amine selected from the group consisting of pyridine, morpholine, quinoline, piperidine, piperazine or derivatives thereof containing one to five C$_1$-C$_8$-alkyl groups.

7. A process as claimed in claim 1, wherein the essential copper oxide catalyst is used on a support material.

8. A process as claimed in claim 7, wherein the inert support is selected from the group consisting of aluminum oxide, silica, titanium oxide, zirconium dioxide, magnesium oxide and oxides of the elements from main groups three and four of the Periodic Table of Elements.

9. A process as claimed in claim 1, wherein the amine is used in an amount of 1 to 10% by weight based on the haloaromatic carbonyl compound.

10. A process as claimed in claim 1, wherein the amine is used in an amount of 1.5 to 5% by weight based on the haloaromatic carbonyl compound.

11. A process as claimed in claimed 1, wherein the copper oxide hydrogenation catalyst consists essentially of a 70 to 100% by weight of copper oxide (I), copper oxide (II) or mixtures thereof, based on the total weight of the catalytically active material.

12. A process as claimed in claim 11, wherein the content of copper oxide in said catalyst is from 85 to 100% by weight.

13. A process as claimed in claim 11, wherein the content of copper oxide in said catalyst is from 95 to 100% by weight.

14. A process as claimed in claim 11, wherein said copper oxide catalyst is supported on an inert support selected from the group consisting of aluminum oxide, silica, titanium oxide, zirconium dioxide, magnesium oxide and oxides of the elements from main groups three and four of the Periodic Table of Elements.

* * * * *

UNITED STATES PATENT AND TRADEMARK OFFICE
CERTIFICATE OF CORRECTION

PATENT NO. : 5,254,752
DATED      : October 19, 1993
INVENTOR(S): Merger et al.

It is certified that error appears in the above-identified patent and that said Letters Patent is hereby corrected as shown below:

Column 5, Claim 1, line 39, change "$C_2$" to --$C_3$--.

Column 5, Claim 1, lines 39 and 40, after "$C_{30}$-", delete "alkoxyalkyl" and substitute --cycloalkylalkyl--.

Signed and Sealed this

Nineteenth Day of April, 1994

Attest:

BRUCE LEHMAN

Attesting Officer    Commissioner of Patents and Trademarks